United States Patent
Sundstrom

(10) Patent No.: US 9,451,906 B2
(45) Date of Patent: Sep. 27, 2016

(54) RETRIEVING MENTAL IMAGES OF FACES FROM THE HUMAN BRAIN

(71) Applicant: International Business Machines Corporation, Armonk, NY (US)

(72) Inventor: Martin Sundstrom, Copenhagen (DK)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 0 days.

(21) Appl. No.: 14/619,228

(22) Filed: Feb. 11, 2015

(65) Prior Publication Data

US 2015/0150492 A1 Jun. 4, 2015

Related U.S. Application Data

(63) Continuation of application No. 12/195,941, filed on Aug. 21, 2008, now Pat. No. 8,989,854.

(51) Int. Cl.
*A61B 5/00* (2006.01)
*A61B 5/117* (2016.01)
*G06F 3/01* (2006.01)
*A61B 5/055* (2006.01)

(52) U.S. Cl.
CPC ............ *A61B 5/1176* (2013.01); *A61B 5/055* (2013.01); *A61B 5/742* (2013.01); *G06F 3/015* (2013.01)

(58) Field of Classification Search
CPC .... A61B 5/055; A61B 5/1176; A61B 5/742; G06F 3/015
See application file for complete search history.

(56) References Cited

U.S. PATENT DOCUMENTS

| 8,989,854 B2* | 3/2015 | Sundstrom | G06F 3/015 600/545 |
| 2005/0154290 A1* | 7/2005 | Langleben | A61B 5/055 600/410 |
| 2005/0273017 A1 | 12/2005 | Gordon | |
| 2007/0299876 A1 | 12/2007 | Welti et al. | |

FOREIGN PATENT DOCUMENTS

WO 02102238 A2 12/2002

OTHER PUBLICATIONS

V. Blanz, et al., "A Morphable Model for the Synthesis of 3D Faces," SIGGRAPH, ACM, 1999, pp. 1-8.
D. Marks, et al. "Multidimensional Representation of Concepts as Cognitive Engrams in the Human Brain," Internet Journal of Neurology, 2007, vol. 6, No. 1, pp. 1-10.
C.J. Solomon, et al., "EigenFIT—The Generation of Photographic-quality facial composites," Journal of Forensic Science, 2004, pp. 1-2.

(Continued)

*Primary Examiner* — Ruth S Smith
(74) *Attorney, Agent, or Firm* — Cantor Colburn LLP; Douglas Lashmit

(57) ABSTRACT

Methods, systems and computer readable storage medium for retrieving mental images of faces from the human brain. An exemplary embodiment includes a method for retrieving mental images of faces from a human brain, the method including generating an image on a screen, measuring brain activity data from a brain scanner, varying characteristics of the image on the screen, detecting changes in the brain activity data measured from the brain scanner, and generating a final image on the screen, the final image being related to a subjectively described mental image.

6 Claims, 2 Drawing Sheets

(56) References Cited

OTHER PUBLICATIONS

Peter J.B. Hancock, et al., "Evolutionary Generation of Faces," Creative Evolutionary Systems, Jul. 2001, pp. 409-423.
C.D. Frowd, et al., "Evolving Human Faces," The Art of Artificial Evolution Natural Computing Series, 2008, pp. 1-20.
C.D. Frowd, et al., "Evolving the Face of a Criminal: How to Search a Face Space More Effectively," ECSIS Symposium on Bio-inspired, Learning, and Intelligent Systems for Security, 2007, pp. 1-8.
Tzu-Pei Grace Chen, et al., "Exploring Gradient-based Face Navigation Interfaces," Proceedings of Graphics Interface 2004, pp. 1-8.
Nature Neuroscience, [online]; [retrieved on Aug. 11, 2008]; retrieved from the Internet http://www.nature.com/neuro/journal/v2/n6/abs/nn0669_574.html N. George, et al., "Contrast Polarity and Face Recognition in the human Fusiform gyrus," Nature Neuroscience, 2, 1999, pp. 574-580.
B. Rossion, et al., "How Does the Brain Discriminate Familiar and Unfamiliar Faces?: A PET Study of Face Categorical Perception," Journal of Cognitive Neuroscience 13:7, 2001, pp. 1019-1034.
S. Gibson, et al., "Innovations in Facial Composite Systems: EigenFIT," Workshop on Eyewitness Identification Evidence, KENT University, 2006, pp. 1-25.
Jiang, et al, "Evaluation of a Shape-Based Model of Human Face Discrimination Using fMRI and Behavioral Techniques," Neuron, Apr. 6, 2006, 50, pp. 159-172.
Loffler, et al., "fMRI Evidence for the Neural Representation of Faces," Nature Neuroscience, vol. 8, No. 10. Oct. 2005, pp. 1386-1390.
R. Gur, et al, "Brain Activation During Facial Emotion Processing," NeuroImage 16, pp. 651-662, 2002.
Whalen, et al., "Masked Presentations of Emotional Facial Expressions Modulate Amygdala Activity without Explicit Knowledge," Journal of Neuroscience, 1998, 18, pp. 411-418.
NoLieMRI.com, [online]; [retrieved on Feb. 11, 2015]; retrieved from the Internet http://www.noliemri.com/ No Lie MRI, "New Truth Verification Technology," No Lie MIR, 2006, pp. 1-1.

\* cited by examiner

RETRIEVING MENTAL IMAGES OF FACES FROM THE HUMAN BRAIN

DOMESTIC PRIORITY

This application is a continuation of U.S. Pat. No. 8,989,854, filed Aug. 21, 2008, the disclosure of which is incorporated by reference herein in its entirety.

BACKGROUND

This invention relates generally to computer imaging, and more particularly to methods, systems and computer program products for retrieving mental images of faces from the human brain.

Having mental images is a subjective quality that can be discussed and conveyed between humans. However, the technology to re-create or communicate mental images are however very primitive and are generally restricted to manual man-made recreations such as drawings. Criminal investigators are limited to using artists to depict persons seen by witnesses. This method is limited by the recall memory of the person but also by the emotional state of the person.

It would be desirable/advantageous to be able to re-create the mental image of a face from the human brain objectively and directly without the need of a subjective interpretation, such as an artist's rendition.

SUMMARY

An exemplary embodiment includes a method for retrieving mental images of faces from a human brain, the method including generating an image on a screen, measuring brain activity data from a brain scanner, varying characteristics of the image on the screen, detecting changes in the brain activity data measured from the brain scanner, and generating a final image on the screen, the final image being related to a subjectively described mental image.

Another exemplary embodiment includes a computer program product for retrieving mental images of faces from a human brain, the computer program product including instructions for causing a computer to implement a method, the method including generating an image on a screen, measuring brain activity data from a brain scanner, varying characteristics of the image on the screen, detecting changes in the brain activity data measured from the brain scanner and generating a final image on the screen, the final image being related to a subjectively described mental image.

A further exemplary embodiment includes a system for retrieving mental images of faces from a human brain, the system including a brain scanner configured to measure brain activity, a screen configured to display an image and a mental facial image retrieval module configured to collect brain activity data from the brain scanner, and configured to vary characteristics of the image on the screen.

BRIEF DESCRIPTION OF THE DRAWINGS

Referring now to the drawings wherein like elements are numbered alike in the several FIGURES.

DETAILED DESCRIPTION

Figure 1:
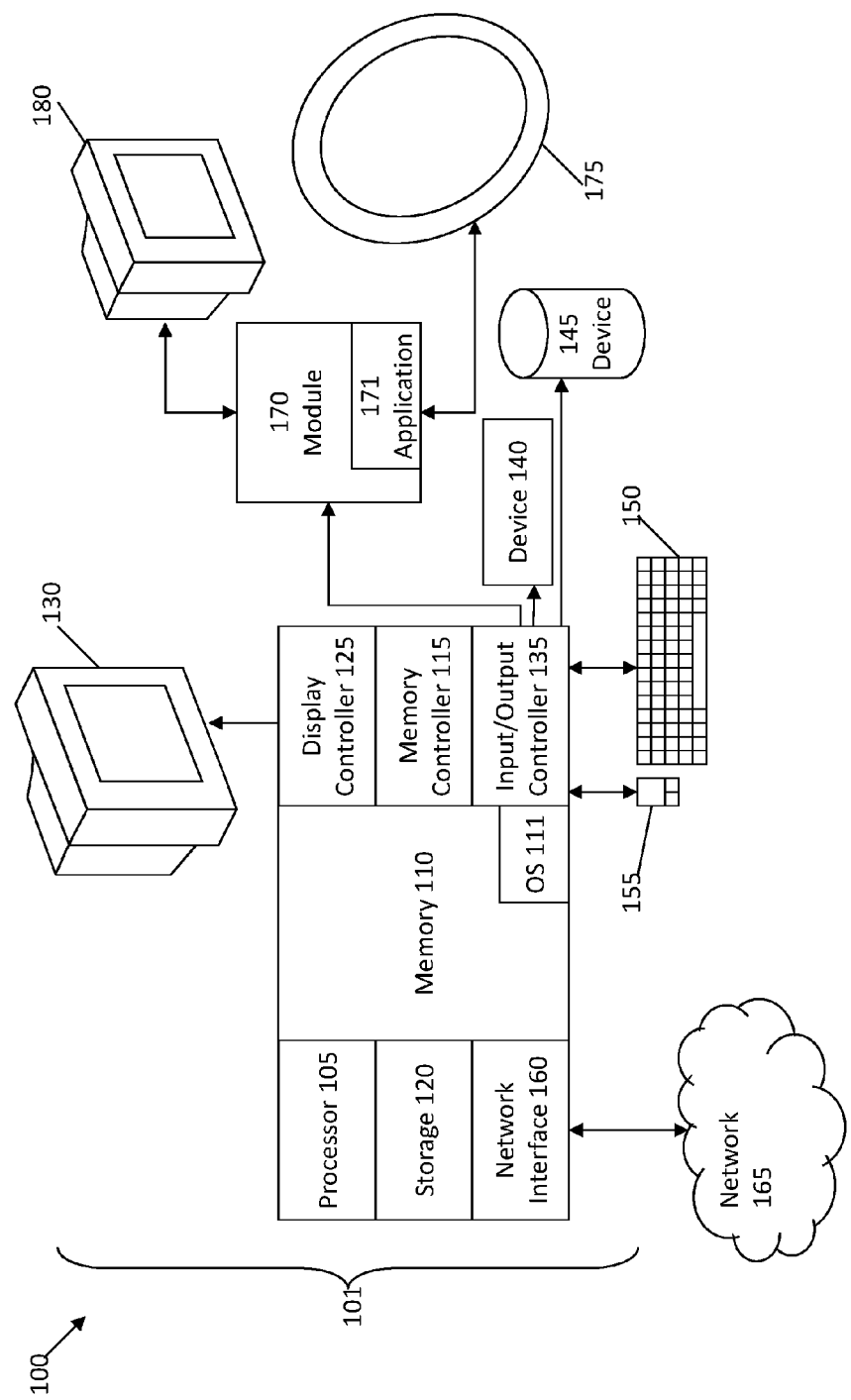
FIG. 1 illustrates an exemplary embodiment of a system for retrieving mental images of faces from the human brain.

Exemplary embodiments include methods, systems and computer program products that retrieve mental images of human faces during emotional circumstances and with an objective precision beyond subjectivity. The methods, systems and computer program products described herein also enable mental retrieval of images from a wide range of larger animals. In exemplary embodiments, the methods, systems and computer program products described herein provide an application interface that can be integrated with an MRI scanner to automatically retrieve mental images, based on brain activity during visualization of an image on a screen. In exemplary embodiments, the methods, systems and computer program products described herein implement recognition memory. In exemplary embodiments, a screen shows a human face that can be varied in all dimensions such as but not limited to hair and eye color, face form or nose form. Current MRI is implemented to detect brain activity in key areas of the brain involved in recognition and retrieval memory such as prefrontal cortex, posterior associative neocortex, medial temporal lobe (specifically the amygdala complex), and most importantly the fusiform gyrus, which respond specifically to familiar faces and with a linearity in activity intensity corresponding to the familiarity. In exemplary embodiments, the facial image on the screen is varied in real time to optimize the response from fusiform gyrus and other areas of the brain under the scrutiny of the MRI. In exemplary embodiments, the temporal resolution of the MRI scanner is a few seconds, which provides an ideal time period for giving the person a few seconds to react to the screen. In exemplary embodiments, the face is varied in real time by feedback from the brain. When the image of the face has been resolved, the activity in the key areas of the brain automatically respond and provide guidelines for the application to form the face until a maximum response is obtained from the fusiform gyrus and amygdala areas. In exemplary embodiments, the process to recreate the mental image can be on the order of minutes, while the face is adjusted to the feedback from the brain every few seconds.

In exemplary embodiments, the methods, systems and computer products described herein can also be implemented on persons in a coma, thereby allowing investigators to retrieve mental images from known persons. However, it is appreciated that because the person is in a coma, there may be little control of what images are retrieved. In addition, it is appreciated that in many cases there may be no activity in the fusiform gyrus. In other forms of coma such as locked-in syndrome, which is a state where the patient is aware and awake but unable to communicate due to complete paralysis of nearly all muscles, the methods, systems and computer program products described herein could obtain facial images from the brain that the person is unable to otherwise express. Locked-in patients sometimes risk not being identified but mistaken for being a coma patient. By asking the patient to think of for example the patients mother and placing the patient in an MRI scanner, the methods, systems and computer program products described herein would be able to identify if the patient's mother appears on the screen. If so, it would be evident that it is possible to communicate with the patient. As such, the methods, systems and computer program products described herein could be used to diagnose locked-in patients.

In exemplary embodiments, the methods, systems and computer program products described herein can evaluate incoming voxel values from a MRI scanner and vary a visual image of a human face in front of the person being investigated. The methods, systems and computer program products described herein control the image on the basis of feedback from the MRI scanner and, as such, functions as an extension to an MRI scanner. The person in the scanner is asked to create a mental image of a face of a person which investigators are trying to ascertain or locate. The image is then morphed in various dimensions until maximum activity is obtained from the fusiform gyrus and amygdala. In exemplary embodiments, when a face starts to resemble the mental image of a face then more amygdala activity is to be expected. As such, unusual quick increases in amygdala activity shows that the methods, systems and computer products described herein have generated characteristics of the image that are close to the actual mental image. As such, variations in the computer generated face become smaller and hence create a more precise facial image. Hence, when recognition is low greater steps in forms can be implemented in an attempt to come closer to the actual mental image. It is therefore appreciated that sensitivity of the methods, systems and computer program products described herein increases when amygdala activity feedback increases. As such, an investigator can first ask whether or not the mental image is a man or a woman. Once established, the investigator could then ask the race of the person in the mental image, and then other features such as basic hair color, eye color and the like. It is appreciated that wide variations of facial images first shown to the person could be limited.

In exemplary embodiments, the methods, systems and computer program products described herein can create an artificial human face on the screen and vary specific features of the face (such as eye size, hair color or face width) dependent on the data the application receives from a brain MRI scanner measuring brain activity from several regions of the brain. In this context, two regions the fusiform gyrus and the amygdala are examined. However, it is appreciated that other areas of the brain can also be examined and can provide further resolution to the generated image. Currently, it has been shown that familiarity of a human face correlates with the intensity of brain activity measured in the fusiform gyrus region in the brain. Emotional arousal is commonly known to correlate with activity in the amygdala region in the brain. In exemplary embodiments, a person is placed in a brain scanner and asked to focus on a mental image of a human face which is to be determined by an application that generates a human face and then varies one feature at a time until brain activity is maximized in the fusiform area and the amygdala. When maximum activity is encountered in the fusiform area and the amygdale (or other areas of the brain), a new facial feature is varied until the examined brain activity is maximized again. In exemplary embodiments, each facial feature is changed with an interval of a few seconds corresponding to the scan time of a brain scanner. When a familiar face is generated by the application then the brain activity in the fusiform region and the amygdala increases, since familiarity creates more emotional response in contrast to a lack of familiarity. When all facial features have been varied and presented to the person in the brain scanner, the generated human face that has generated the most brain activity in the fusiform and amygdala area is an image close to the person's mental image. In this way the methods, systems and computer program products described herein can be used to in an objective manner to measure the brain response from a person when seeing an image. The maximization in the brain activity correlating with the facial features circumvents any subjective interferences of the person can since activity response from the fusiform region is autonomous and can not be controlled by the will of the person. The image could then be shown to the person who can be asked if the image is correct.

FIG. 1 illustrates an exemplary embodiment of a system 100 for retrieving mental images of faces from the human brain. The methods described herein can be implemented in software (e.g., firmware), hardware, or a combination thereof. In exemplary embodiments, the methods described herein are implemented in software, as an executable program, and is executed by a special or general-purpose digital computer, such as a personal computer, workstation, minicomputer, or mainframe computer. The system 100 therefore includes general-purpose computer 101.

In exemplary embodiments, in terms of hardware architecture, as shown in FIG. 1, the computer 101 includes a processor 105, memory 110 coupled to a memory controller 115, and one or more input and/or output (YO) devices 140, 145 (or peripherals) that are communicatively coupled via a local input/output controller 135. The input/output controller 135 can be, for example but not limited to, one or more buses or other wired or wireless connections, as is known in the art. The input/output controller 135 may have additional elements, which are omitted for simplicity, such as controllers, buffers (caches), drivers, repeaters, and receivers, to enable communications. Further, the local interface may include address, control, and/or data connections to enable appropriate communications among the aforementioned components.

The processor 105 is a hardware device for executing software, particularly that stored in memory 110. The processor 105 can be any custom made or commercially available processor, a central processing unit (CPU), an auxiliary processor among several processors associated with the computer 101, a semiconductor based microprocessor (in the form of a microchip or chip set), a macroprocessor, or generally any device for executing software instructions.

The memory 110 can include any one or combination of volatile memory elements (e.g., random access memory (RAM, such as DRAM, SRAM, SDRAM, etc.)) and nonvolatile memory elements (e.g., ROM, erasable programmable read only memory (EPROM), electronically erasable programmable read only memory (EEPROM), programmable read only memory (PROM), tape, compact disc read only memory (CDROM), disk, diskette, cartridge, cassette or the like, etc.). Moreover, the memory 110 may incorporate electronic, magnetic, optical, and/or other types of storage media. Note that the memory 110 can have a distributed architecture, where various components are situated remote from one another, but can be accessed by the processor 105.

The software in memory 110 may include one or more separate programs, each of which comprises an ordered listing of executable instructions for implementing logical functions. In the example of FIG. 1, the software in the memory 110 includes the mental facial image retrieval methods described herein in accordance with exemplary embodiments and a suitable operating system (OS) 111. The operating system 111 essentially controls the execution of other computer programs, such the mental facial image retrieval systems and methods described herein, and provides scheduling, input/output control, file and data management, memory management, and communication control and related services.

The mental facial image retrieval methods described herein may be in the form of a source program, executable program (object code), script, or any other entity comprising a set of instructions to be performed. When a source program, then the program needs to be translated via a compiler, assembler or an interpreter, which may or may not be included within the memory 110, so as to operate properly in connection with the OS 111. Furthermore, the mental facial image retrieval methods can be written as an object oriented programming language, which has classes of data and methods, or a procedure programming language, which has routines, subroutines, and/or functions.

In exemplary embodiments, a conventional keyboard 150 and mouse 155 can be coupled to the input/output controller 135. Other devices such as the devices 140, 145 may include input devices, for example but not limited to a printer, a scanner, microphone, and the like. Finally, the devices 140, 145 may further include devices that communicate both inputs and outputs, for instance but not limited to, a network interface card (NIC) or modulator/demodulator (for accessing other files, devices, systems, or a network), a radio frequency (RF) or other transceiver, a, telephonic interface, a bridge, a router, and the like. The system 100 can further include a display controller 125 coupled to a display 130. In exemplary embodiments, the system 100 can further include a network interface 160 for coupling to a network 165. The network 165 can be an IP-based network for communication between the computer 101 and any external server, client and the like via a broadband connection. The network 165 transmits and receives data between the computer 101 and external systems. In exemplary embodiments, network 165 can be a managed IP network administered by a service provider. The network 165 may be implemented in a wireless fashion, e.g., using wireless protocols and technologies, such as WiFi, WiMax, etc. The network 165 can also be a packet-switched network such as a local area network, wide area network, metropolitan area network, Internet network, or other similar type of network environment. The network 165 may be a fixed wireless network, a wireless local area network (LAN), a wireless wide area network (WAN) a personal area network (PAN), a virtual private network (VPN), intranet or other suitable network system and includes equipment for receiving and transmitting signals.

If the computer 101 is a PC, workstation, intelligent device or the like, the software in the memory 110 may further include a basic input output system (BIOS) (omitted for simplicity). The BIOS is a set of essential software routines that initialize and test hardware at startup, start the OS 111, and support the transfer of data among the hardware devices. The BIOS is stored in ROM so that the BIOS can be executed when the computer 101 is activated.

When the computer 101 is in operation, the processor 105 is configured to execute software stored within the memory 110, to communicate data to and from the memory 110, and to generally control operations of the computer 101 pursuant to the software. The mental facial image retrieval methods described herein and the OS 111, in whole or in part, but typically the latter, are read by the processor 105, perhaps buffered within the processor 105, and then executed.

When the systems and methods described herein are implemented in software, as is shown in FIG. 1, the methods can be stored on any computer readable medium, such as storage 120, for use by or in connection with any computer related system or method. In the context of this document, a computer readable medium is an electronic, magnetic, optical, or other physical device or means that can contain or store a computer program for use by or in connection with a computer related system or method. Mental facial image retrieval methods described herein can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In exemplary embodiments, a "computer-readable medium" can be any means that can store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium. More specific examples (a non-exhaustive list) of the computer readable medium would include the following: an electrical connection (electronic) having one or more wires, a portable computer diskette (magnetic), a random access memory (RAM) (electronic), a read-only memory (ROM) (electronic), an erasable programmable read-only memory (EPROM, EEPROM, or Flash memory) (electronic), an optical fiber (optical), and a portable compact disc read-only memory (CDROM) (optical). Note that the computer-readable medium could even be paper or another suitable medium upon which the program is printed, as the program can be electronically captured, via for instance optical scanning of the paper or other medium, then compiled, interpreted or otherwise processed in a suitable manner if necessary, and then stored in a computer memory.

In exemplary embodiments, where the mental facial image retrieval methods are implemented in hardware, the mental facial image retrieval methods described herein can implemented with any or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

In exemplary embodiments, the system 100 can further include mental facial image retrieval devices coupled to the I/O controller 135. In exemplary embodiments, the mental facial image retrieval devices can include a mental facial image retrieval module 170 coupled to the I/O controller 135. In exemplary embodiments, the system 100 can further include an MRI scanner 175 coupled to the mental facial image retrieval module 170. The system 100 can further include an image generation screen 180 coupled to the mental facial image retrieval module 170. In exemplary embodiments, the mental facial image retrieval module 170 can include a mental facial image retrieval application 171 that can be operatively coupled to the processor 105. In exemplary embodiments, as described herein, the application 171 is responsible for monitoring the brain activity collected from the MRI scanner 175 and to generate and modify facial images on the image generation screen 180.

The following description provides a general example of the methods, systems and computer program products described herein. A person is placed in a brain scanner (e.g., the scanner 175) and asked to think of the human face of interest. This first step can be crucial because familiarity with other faces may create false positives in certain facial characteristics on the screen 180. In such a case, the person in the scanner can simply state that the face being generated is a false positive. Next, the application 171 generates a basic human face on the screen 180 based on general description, such as a male. A feature of the face (e.g., the facial characteristics) is varied in a limited number of states for example blue, brown, green, grey, black as for eye color. For each color the brain activity in the fusiform and amygdala is measured by the brain scanner 175 and passed along to the application 171. If the greatest increase in brain activity is measured for blue eyes, this feature (i.e., blue eyes) is kept (i.e., fixed in the image that will be a final generated image) and another feature is then varied such as hair color. When a maximum of brain activity in the relevant regions of the brain has been obtained then this feature (e.g., brown hair) is kept and another varied until all features have been examined. It is appreciated that other such facial features can include but are not limited to, nose shape, eye shape, cheek bone shape, skin tone, forehead shape and chin shape.

The application 171 can generate the facial image in a variety of ways. For example, a start image is constructed from overall input such as the person in the mental image being described as a male. For each scan the application 171 receives input from the scanner 175 and analyses the brain activity in selected regions. (It is appreciated that a spatial normalization of the persons head has been done in advance in order to calibrate brain function and brain regions. When the facial characteristic has been varied for all values related to the facial characteristic (e.g., different hues of blue eyes, different shades of brown hair) resulting in the highest brain activity, the varied facial characteristic is retained and fixed in the final image and a new feature is varied. When no more features are left, the examination is done and the application 171 generates an image of a human face that has generated the overall most activation in the fusiform and amygdala region for each of the facial characteristics present in the final facial image.

In exemplary embodiments, the methods systems and computer program products described herein can also perform a spatial normalization before the procedures described herein. As such, MRI or PET scans may be performed in order to obtain spatial normalization. In addition, for the methods described herein the output from the scanner 175 are performed real time, in which a piece of software obtains the voxel data from the scanner 175, performs a spatial normalization and subtracts background activity. This background activity or initial brain activity is a baseline level from which all measurements are evaluated. The baseline level should be obtained from the initial image that is generated in the beginning. During measurement, every image change causes a change in the fusiform activity. This change is evaluated and compared to the previous activity. In exemplary embodiments, the evaluation and comparison are performed in two dimensions. In addition, activity level and spatial location are also evaluated and compared. In exemplary embodiments, the methods, systems and computer program products described herein maximize spatial density of activity and activity levels and always with the original image as baseline. Normally, normalization is done by a human after scanning. In exemplary embodiments, one spatial normalization can be performed by a human in the beginning of the process. The result can then be fed the result into the application 171 to enable the application 171 to normalize all scans.

In exemplary embodiments, the methods, systems and computer program products perform additional operations such as baselines and familiarity calibration. For baselines, a brain scan is performed in order to measure normal brain activity in the scanner 175. This activity is then subtracted from all measured data in order to isolate activity related to viewing an image of a human face. For familiarity calibrations, in order to estimate the degree of familiarity, the person in the scanner 175 is shown an image of a familiar person on the screen 180, such as a parent. The activity measured in the amygdala and fusiform represents brain activity levels corresponding to a very familiar person. This level can be used to evaluate the relative degree of familiarity of the human face generated by the application 171. It is therefore appreciated that when a similar level of brain activity corresponding to familiarity is generated when the person is shown facial characteristics related to the mental image of interest, the system 100 can then know that familiarity has been achieved and the facial characteristic can be fixed for the final image.

Figure 2:
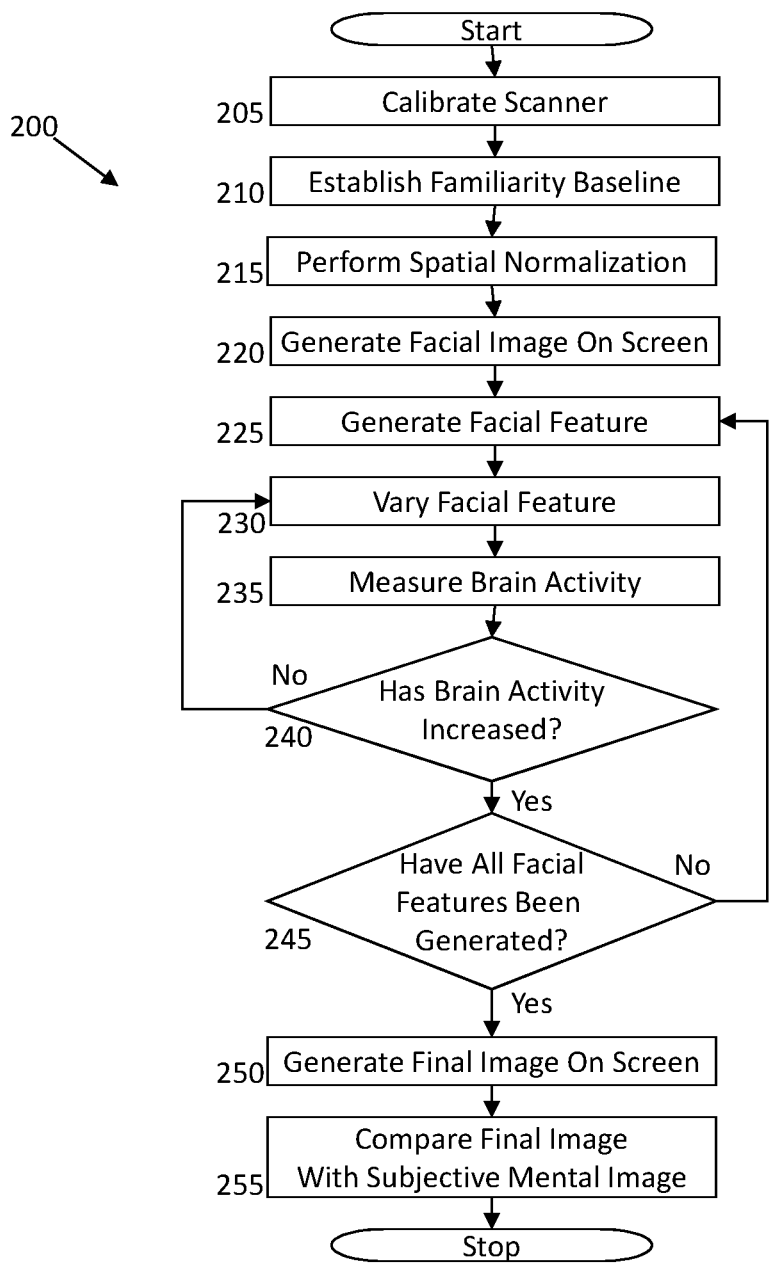
FIG. 2 illustrates a flow chart of a method for retrieving mental images of faces from the human brain in accordance with exemplary embodiments.

FIG. 2 illustrates a flow chart of a method for retrieving mental images of faces from the human brain in accordance with exemplary embodiments. At block 205, the scanner 175 is calibrated. At block 210, the system 100 establishes a familiarity baseline. At block 215, the system 100 performs a spatial normalization. In exemplary embodiments, the spatial normalization calibrates the application 171 such that the application 171 can spatial normalize all scans and decide if activity comes from the fusiform area, amygdala or other areas of the brain. At block 220, the system 100 can then generate a facial image on the screen 180. At block 225, the system 100 can generate a facial feature on the facial image on the screen 180. At block 230, the system 100 can vary the facial feature. At block 240, the system 100 can detect whether there has been an increase in the brain activity. If not, then the system 100 can continue to vary the facial feature at block 230 until the pre-determined increase in brain activity has been measured. If at block 240, the brain activity has increased, then at block 245, the system 100 determines if all facial features have been generated. If not, then at block 225 another facial features is generated. It is appreciated that the methods, systems and computer program products described herein can generate any number of facial features and the total number of facial features can vary depending on the nature of the investigation, the nature of the mental image and other factors. Once all facial features have been generated at block 245, then the system 100 at block 250 generates the final image on the screen 180. At block 255, the final image can be compared to the mental image. In exemplary embodiments, the comparison can be made by asking the person if the generated image is correct.

Technical effects and benefits include the ability to solve the problem of retrieving mental images of human faces during hard emotional circumstances and with a precision that goes beyond subjectivity. Furthermore, the methods, systems and computer program products described herein enable mental retrieval of images from a wide range of larger animals. The methods, systems and computer program products described herein can potentially be used for retrieving mental images of human faces in person exposed to a crime but there is potentially also a huge more commercial marked for retrieving mental images of human faces in private consumers wishing for obtaining an image of a human face from a specific event. The methods, systems and computer program products described herein establish a closed loop control between application and the subject's brain (i.e. the subjects' responses don't guide the application). As described above, the methods, systems and computer program products described herein implement the activity of the fusiform gyrus. A computer application uses these biological data acquired through a Brain-Machine interface. The subject's brain activity establishes a closed-loop control with an application, by guiding the application decisions which in turn modifies the subject's brain activity. The application shows a composite picture of human features (as collected from a human features database or through a morphing program) to the subject. This action elicits a response in the subject's fusiform gyrus. This response is detected, processed and feedback to the application which at this point makes a decision according to a given search algorithm. The decision changes a feature or group of features from the composite image with the objective of maximizing the activity of the subject's fusiform gyrus. An exemplary embodiment considers MRI, but any other suitable means to detect the activity in the fusiform gyrus can be implemented.

As described above, the embodiments of the invention may be embodied in the form of computer-implemented processes and apparatuses for practicing those processes. Embodiments of the invention may also be embodied in the form of computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. The present invention can also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another.

The invention claimed is:

1. A non-transitory, computer readable storage medium having computer readable instructions stored thereon that, when executed by a computer, implement a method for retrieving mental images of faces from a human brain, the method comprising:
generating an initial human facial image on a screen, the initial human facial image including characteristics based on an initial description of a human face;
measuring brain activity data from a brain scanner, the brain activity data being measured from a subject viewing the screen;
varying the characteristics of the initial human facial image on the screen;
detecting changes in the brain activity data measured from the brain scanner, the brain activity indicative of recognizing the human face;
fixing certain characteristics that correspond to brain activity that indicated strong recognition of the certain characteristics to construct a final human facial image, constructing the final human facial image from the certain characteristics that have been fixed based on the brain activity that indicated strong recognition of the certain characteristics; and
generating the final human facial image on the screen, the final human facial image including the certain characteristics that have been fixed;
wherein varying characteristics of the initial human facial image on the screen comprises:
varying a first facial characteristic and varying a second facial characteristic;
wherein the fixing comprises:
in response to varying the first facial characteristic that results in an increase of brain activity as indicated from the brain activity data, fixing, based upon the increase of the brain activity associated with the first facial characteristic, the first facial characteristic as part of the final human facial image on the screen; and
in response to varying the second facial characteristic that results in an increase of brain activity as indicated from the brain activity data, fixing, based upon the increase of the brain activity associated with the second facial characteristic, the second facial characteristic as part of the final human facial image on the screen.

2. The storage medium of claim 1, wherein the brain activity data from the brain scanner is activity from areas of a human brain related to facial recognition.

3. The storage medium of claim 2, wherein the areas of the human brain include at least one of prefrontal cortex, posterior associative neocortex, medial temporal lobe, amygdala complex, and fusiform gyms.

4. The storage medium of claim 2, wherein detecting changes in the brain activity data measured from the brain scanner comprises an increase of brain activity from areas of the human brain related to facial recognition.

5. A system for retrieving mental images of faces from a human brain, the system comprising:
a processor, wherein the processor is operatively coupled to a mental facial image retrieval module;
a brain scanner configured to measure brain activity and changes in brain activity indicative of recognizing a human face;
a screen configured to display an initial human facial image including characteristics based on an initial description of the human face, and a final human facial image that includes updated characteristics based on predetermined brain activity indicative of recognizing the human face; and
wherein the processor, being operatively coupled to the mental facial image retrieval module, is configured to collect brain activity data from the brain scanner, and configured to vary characteristics of the initial human facial image on the screen and further configured to fix certain characteristics that correspond to brain activity that indicated strong recognition of the certain characteristics to reconstruct a final human facial image, and reconstruct a final human facial image from the certain characteristics that have been fixed based on the strong recognition evidenced by the brain activity that indicated strong recognition of the certain characteristics;
wherein varying characteristics of the initial human facial image on the screen comprises:
varying a first facial characteristic and a second facial characteristic;
wherein the fixing comprises:
in response to varying the first facial characteristic that results in an increase of brain activity as indicated from the brain activity data, fixing, based on the increase in the brain activity associated with the first facial characteristic, the first facial characteristic as part of the final human facial image on the screen; and in response to varying the second facial characteristic that results in an increase of brain activity as indicated from the brain activity data, fixing, based on the increase of the brain activity associated with the second facial characteristic, the second facial characteristic as part of the final human facial image on the screen.

6. The system of claim 5, wherein the brain scanner is an MRI scanner.

* * * * *